US008094588B2

(12) United States Patent
Sako et al.

(10) Patent No.: US 8,094,588 B2
(45) Date of Patent: Jan. 10, 2012

(54) INFORMATION TRANSMISSION METHOD, INFORMATION TRANSMISSION APPARATUS, INFORMATION RECORDING OR REPRODUCING METHOD, INFORMATION RECORDING OR REPRODUCING APPARATUS AND RECORDING MEDIUM

(75) Inventors: Yoichiro Sako, Tokyo (JP); Masayoshi Miura, Chiba (JP); Susumu Yabe, Tokyo (JP); Motoyuki Takai, Tokyo (JP); Akiko Inoue, Saitama (JP)

(73) Assignee: Sony Corporation (JP)

( * ) Notice: Subject to any disclaimer, the term of this patent is extended or adjusted under 35 U.S.C. 154(b) by 709 days.

(21) Appl. No.: 10/541,278

(22) PCT Filed: Dec. 11, 2003

(86) PCT No.: PCT/JP03/15885
§ 371 (c)(1),
(2), (4) Date: Jul. 1, 2005

(87) PCT Pub. No.: WO2004/066264
PCT Pub. Date: Aug. 5, 2004

(65) Prior Publication Data
US 2006/0083218 A1    Apr. 20, 2006

(30) Foreign Application Priority Data
Jan. 17, 2003 (JP) .............................. P2003-009646

(51) Int. Cl.
*H04L 5/22* (2006.01)
(52) U.S. Cl. ......................................... 370/265; 370/493
(58) Field of Classification Search .................. 370/271, 370/260–264, 265
See application file for complete search history.

(56) References Cited

U.S. PATENT DOCUMENTS

| 4,151,373 | A | * | 4/1979 | Widmer et al. ............... 370/514 |
| 5,564,433 | A | * | 10/1996 | Thornton ....................... 600/544 |
| 5,795,306 | A | | 8/1998 | Shimotani et al. |
| 6,236,884 | B1 | | 5/2001 | Hunter et al. |

(Continued)

FOREIGN PATENT DOCUMENTS

EP  0959607  11/1999

(Continued)

OTHER PUBLICATIONS

Sundberg, et al., "Short-term variation of subglottal pressure for expressive purposes in signing and stage speech: a preliminary investigation.", Journal of Voice: Official Journal of the Voice Foundation, 7(3):227-234 (1993).

(Continued)

*Primary Examiner* — Ricky Ngo
*Assistant Examiner* — Ben Liu
(74) *Attorney, Agent, or Firm* — Lerner, David, Littenberg, Krumholz & Mentlik, LLP

(57) ABSTRACT

An information transmission method capable of reproducing the atmosphere of a concert hall or a live performance hall, wherein bio-information of a speaker, player, actor or conductor, who serves as a source of speech, sounds or music and/or bio-information of a performer included within an image are multiplexed with respect to information of speech or music and/or information of the image for transmission thereof. At the receiving side, sense stimulation based on the bio-information is provided to the viewer, or information of speech or music and/or information of the image are controlled on the basis of the bio-information to thereby reproduce presence or live appeal.

46 Claims, 8 Drawing Sheets

U.S. PATENT DOCUMENTS

| | | |
|---|---|---|
| 6,415,188 B1 | 7/2002 | Fernandez et al. |
| 6,922,664 B1 * | 7/2005 | Fernandez et al. ............... 703/13 |
| 7,188,151 B2 * | 3/2007 | Kumar et al. ................. 709/217 |
| 7,376,159 B1 * | 5/2008 | Stanger et al. ................. 370/528 |
| 2001/0044588 A1 * | 11/2001 | Mault ........................... 600/549 |
| 2002/0143241 A1 * | 10/2002 | Thorell ......................... 600/300 |
| 2005/0078195 A1 * | 4/2005 | VanWagner ............... 348/231.3 |
| 2006/0258446 A1 * | 11/2006 | Nguyen et al. ................... 463/30 |

FOREIGN PATENT DOCUMENTS

| | | |
|---|---|---|
| JP | 63-300772 | 12/1988 |
| JP | 01-162069 A | 6/1989 |
| JP | 03-163498 A | 7/1991 |
| JP | 11-004892 A | 1/1999 |
| JP | 2000-152207 A | 5/2000 |
| JP | 2000-294389 | 10/2000 |
| JP | 2001-057672 | 2/2001 |
| JP | 2001-169309 A | 6/2001 |
| JP | 2001-195060 | 7/2001 |
| JP | 2001346768 A | 12/2001 |
| JP | 2002-027453 A | 1/2002 |
| JP | 2002-099202 A | 4/2002 |
| JP | 2002-159099 A | 5/2002 |
| JP | 2002-239265 A | 8/2002 |
| JP | 2003-111106 | 4/2003 |
| JP | 2003-248768 | 9/2003 |
| WO | 9957896 | 11/1999 |

OTHER PUBLICATIONS

Supplementary European Search Report from corresponding European Application 03 77 8826.2, dated Apr. 1, 2009.

* cited by examiner

INFORMATION TRANSMISSION METHOD, INFORMATION TRANSMISSION APPARATUS, INFORMATION RECORDING OR REPRODUCING METHOD, INFORMATION RECORDING OR REPRODUCING APPARATUS AND RECORDING MEDIUM

CROSS-REFERENCE TO RELATED APPLICATIONS

The present application is a national stage application under 35 U.S.C. §371 of International Application No. PCT/JP03/15885, filed Dec. 11, 2003, which claims priority from Japanese Application No. JP 2003-009646, filed Jan. 17, 2003, the disclosures of which are hereby incorporated by reference herein.

BACKGROUND OF THE INVENTION

1. Technical Field

The present invention relates to a method for performing transmission of, e.g., information of speech (sound) and/or music, and/or information of image and an apparatus therefor, relates to an information recording or reproducing method and an information recording or reproducing apparatus, and relates to a recording medium.

2. Background Art

Hitherto, there have been performed methods to record information of music or image at classic concert or jazzing live performance, etc. onto recording medium such as CD (Compact Disc) or DVD (Digital Versatile Disc), etc., or to perform transmission of such music or image information by a method such as broadcast, etc.

Even if information obtained by reproducing information of music or image recorded on the CD or DVD is viewed, or even if live broadcasting program of live performance is viewed, reproduction in such viewing form is far from live appeal which has been actually viewed at the concert hall or the live hall. It is considered that the atmosphere of the concert hall or the live hall is not directly transmitted to viewers for reproduction information and/or viewers for broadcasting program.

For this reason, even if, e.g., the technology of the Japanese Patent Application Laid Open No. 2001-57672 is used to detect, as bio-information (bioinformation), feeling with respect to reproduction information or broadcasting program of viewer of the reproduction information or viewer of the broadcasting program to control the reproduction information or the broadcasting information on the basis of the detection output, it is impossible to reproduce the atmosphere of the concert hall or the live hall. The reason thereof is that viewer of reproduction information and/or viewer of broadcasting program do not exist at the concert hall or the live hall.

As stated above, hitherto, even if live sound recording is performed, or live program is broadcasted, it was impossible to transmit the atmosphere of the concert hall or live hall at the time of reproduction of the live sound recording or to viewers of the live program.

SUMMARY OF THE INVENTION

An object of the present invention is to provide a novel information transmission method and a novel information transmission apparatus, a novel information recording or reproducing method and a novel information recording or reproducing apparatus, and a novel recording medium which can solve the problems that prior arts as described above have.

The present invention is directed to an information transmission method of performing transmission of audio information and/or video (image) information in the state where bio-information of a participator present at the place where those information are acquired is multiplexed with respect to the audio information and/or the video information.

Here, the participator is speaker, player, actor or conductor who serves as providing (sending) source of audio information, and/or performer (actor, actress) or photographed person included in image.

Further, listener present at the place where audio information is acquired and/or viewing person present at the place where video information is acquired are included in the participator.

In the information transmission method according to the present invention, transmission of bio-information is performed in a manner associated with audio information and/or video information corresponding to a timing where the bio-information has been caused to take place. Here, audio information and/or video information, and bio-information are partitioned every time period of the same predetermined time length, and transmission of the partitioned bio-information is performed in synchronism with audio information and/or video information of corresponding predetermined time length period.

Moreover, audio information and/or video information may be partitioned every time period of a predetermined time length to perform statistical processing of bio-information at plural time periods of the predetermined time length to calculate statistical bio-information (statistically processed bio-information) to perform transmission of the statistical bio-information in synchronism with audio information and/or video information of plural time periods of corresponding predetermined time length.

In the information transmission method according to the present invention, the bio-information is at least one of body motion (movement), myoelectricity, body surface temperature, skin sweating, skin resistance, pulse, breath, microvibration, cardioelectricity, heartbeat, and blood pressure.

The bio-information is extracted from audio information and/or video information. Transmission of the bio-information thus extracted is performed along with audio information and/or video information.

The information transmission apparatus according to the present invention comprises: information acquiring means for acquiring audio information and/or video information; bio-information detecting means for detecting bio-information of a participator present at the place where these information are acquired; and transmission means for performing transmission of the audio information and/or the video information which have been obtained from the information acquiring means and the bio-information which has been obtained from the bio-information detecting means.

The information recording method according to the present invention comprises: recording, with respect to a predetermined recording medium, audio information and/or video information, and bio-information of a participator present at the place where these information are acquired.

The recording medium used in the information recording method according to the present invention is at least one of optical disc, magnetic tape, hard disc and semiconductor memory.

In the information recording method according to the present invention, the bio-information is extracted from audio information and/or video information, and the bio-information thus extracted is recorded along with the audio information and/or the video information.

The information recording apparatus according to the present invention comprises: information acquiring means for acquiring audio information and/or video information; bio-information detecting means for detecting bio-information of a participator present at the place where these information are acquired; and recording means for recording, with respect to a predetermined recording medium, the audio information and/or the video information which have been obtained from the information acquiring means and the bio-information which has been obtained from the bio-information detecting means.

In the information recording apparatus according to the present invention, the recording means records bio-information with respect to the recording medium along with audio information and/or video information corresponding to a timing where the bio-information has been caused to take place.

The recording means serves to partition audio information and/or video information, and bio-information every time period of the same predetermined time length to record the bio-information thus partitioned along with audio information and/or video information of corresponding predetermined time length period.

Further, the recording means serves to partition audio information and/or video information every time period of a predetermined time length to perform statistical processing of bio-information at plural time periods of the predetermined time length to calculate statistical bio-information to record the statistical bio-information along with audio information and/or video information of plural time periods of the corresponding predetermined time length.

As the recording medium, there is used at least one of optical disc, magnetic tape, hard disc and semiconductor memory.

The bio-information detecting means serves to extract bio-information from audio information and/or video information.

The information reproducing method according to the present invention comprises: reproducing audio information and/or video information to offer the information thus obtained to user, and to give, to the user, sense stimulation based on bio-information of a participator present at the place where the audio information and/or the video information are acquired.

In the information reproducing method according to the present invention, audio information and/or video information, and bio-information are received through a transmission medium.

Here, the audio information and/or the video information, and the bio-information are read out from the recording medium.

In the information reproducing method according to the present invention, the participator is a listener present at the place where audio information is acquired and/or a viewing person present at the place where video information is acquired, whereby the audio information and/or the video information are controlled on the basis of bio-information of the participator present at the place where the audio information and/or the video information are acquired to reproduce those information. Here, the audio information and/or the video information and the bio-information are received through transmission medium.

The information reproducing apparatus according to the present invention comprises: means for reproducing audio information and/or video information to offer the information thus reproduced to user; and means for giving, to the user, sense stimulation based on bio-information of a participator present at the place where the audio information and the video information are acquired.

The information reproducing apparatus further comprises receiving means for receiving audio information and/or video information, and bio-information through a transmission medium.

The information reproducing apparatus according to the present invention comprises: means for reading out, from a receiving medium, audio information and/or video information, and bio-information.

The information reproducing apparatus according to the present invention comprises reproducing means for controlling audio information and/or video information on the basis of bio-information of a participator present at the place where the audio information and/or video information are acquired to reproduce those information. In the information reproducing apparatus, there is provided receiving means for receiving audio information and/or video information, and bio-information through a transmission medium. Moreover, the information reproducing apparatus comprises means for reading out, from the recording medium, audio information and/or video information, and bio-information.

The present invention is directed to a recording medium, and is adapted so that audio information and/or video information, and bio-information of a participator present at the place where these information are acquired are recorded.

Still further objects of the present invention and practical merits obtained by the present invention will become more apparent from the description of the embodiments which will be given below with reference to the attached drawings.

DETAILED DESCRIPTION

BEST MODE FOR CARRYING OUT THE INVENTION

The information transmission method and the information transmission apparatus, the information recording method and the information recording apparatus, and information reproducing method and information reproducing apparatus according to the present invention, and recording medium according to the present invention will now be described in practical sense with reference to the attached drawings.

The information recording method and the information recording apparatus according to the present invention which will be explained below are caused to perform, through Internet, transmission of information of speech (sound) or music (hereinafter simply referred to as music information for the brevity of explanation) which have been recorded at the classic concert.

Figure 1:
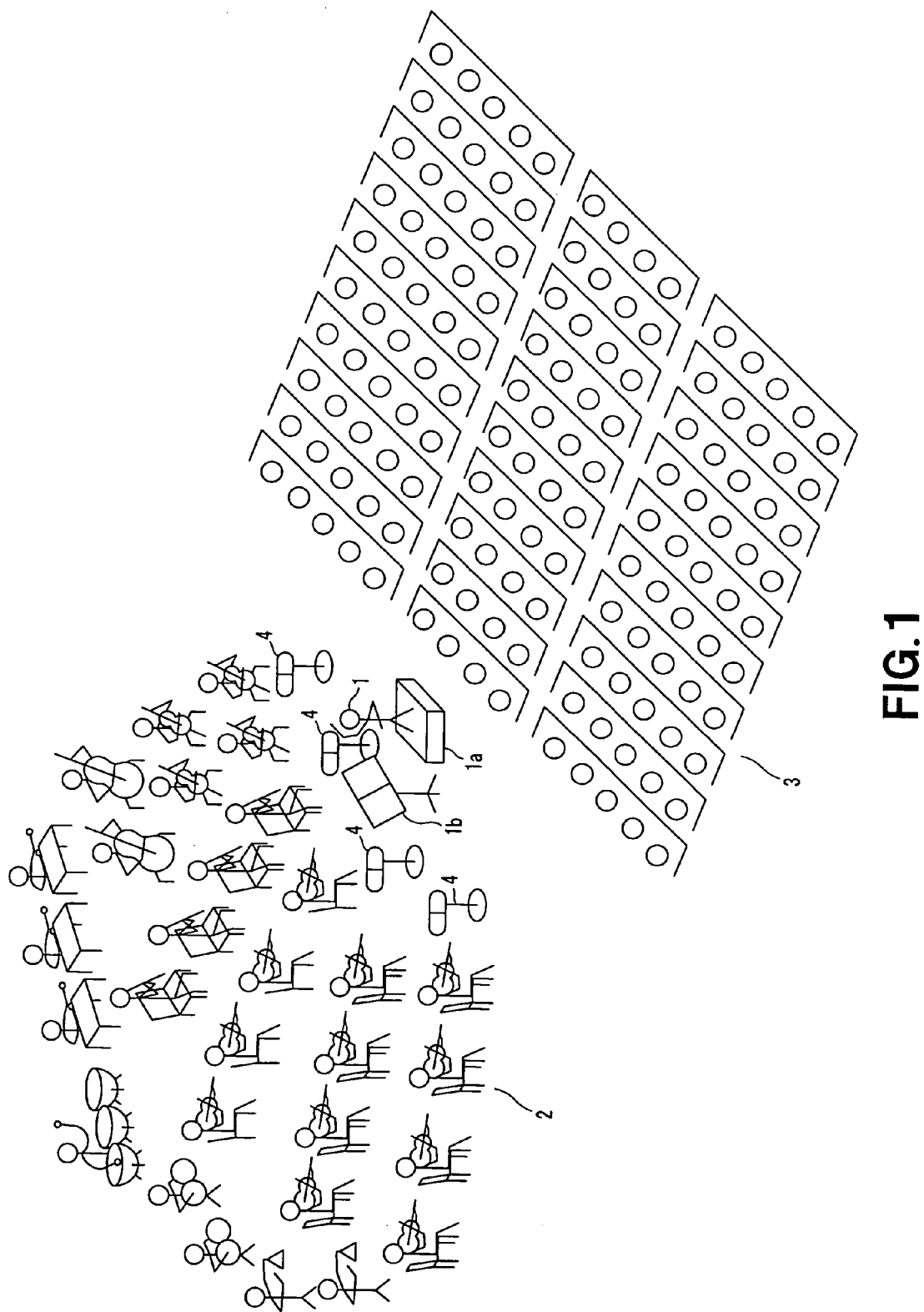
FIG. 1 is a view for explaining the environment to which an information transmission apparatus according to the present invention is applied.

FIG. 1 is a view showing an example of the state of a concert hall. A conductor 1 waves baton, and listeners 3 listen to performance of an orchestra 2. Further, plural microphones 4 are installed (provided) at suitable positions as sound collection of music information of respective channels such as center channel, left channel and right channel, etc., and serve to collect sounds of music by performance of the orchestra.

In the method and the apparatus for recording information according to the present invention, in order to transmit atmosphere of the concert, bio-information such as body motion (movement), breath, pulse, blood pressure, body surface temperature, skin sweating and/or skin resistance, etc. of the conductor 1, a predetermine player, e.g., concert master, etc. of the orchestra 2, and listener of, e.g., best listening position located at a predetermined position among listeners 3 are detected to perform transmission of those bio-information along with music information.

For example, it is general that, e.g., body motion (movement) or breath of the conductor is synchronized with rhythm or tempo, etc. of music to be played or performed. It is deemed that when, e.g., there is a desire to conduct performance of slow melody, body motion and/or breath become slow in harmony therewith, and when shift to big sound is suddenly performed, body motion becomes great in harmony therewith, and breathing also changes in harmony therewith such that breath is once stopped to shift from inspiration to expiration at a stroke.

It is expected that, at the part of rhythm or tempo suddenly changing, body motion and/or breath of player suddenly change in harmony therewith, and at the slow melodious part, body motion and/or breath slowly change in harmony therewith. It is considered that when shift to big sound is suddenly performed, great changes may be performed at a stroke with respect to body motion and/or breath in the state where attention is drawn to baton of the conductor.

It is considered that in the case where player such as singer, etc., exists, that player is also caused to undergo body motion in accordance with rhythm of music or image in music, etc., whereby information of that breathing (breath) gives presence.

Further, it is considered that there is performed a change such that pulse and/or heartbeat become many and skin sweating becomes many at the music part where mood is raised or enhanced, and pulse and/or heartbeat slowly become stable at slow music part.

It is expected that if information of breathing and/or body motion of conductor, player and/or actor or actress, and/or emotional information of listeners which have been stated above can be transmitted to the side of listener who listens to information obtained by receiving transmitted audio information to reproduce them, presence of live performance can be transmitted as it is.

In view of the above, in the present invention, e.g., acquisition of bio-information which will be explained below is performed.

First, a biosensor (body motion sensor) for detecting body motion or movement of the conductor is provided at, e.g., a conductor table 1a on which the conductor 1 stands up. Moreover, biosensor (breath sensor) for detecting breath of the conductor is provided at, e.g., the conductor table 1a or a score table 1b.

For example, the body motion can be detected by a method using optical sensor, or a method of detecting motion information of image with respect to picked up image from image pick-up device, etc. Since breath has frequency component of a relatively low specific range, e.g., microphone is embedded at the conductor table 1a or the score table 1b of the conductor 1, or microphone is embedded at the back side of a watch that the conductor 1 attaches to detect vibration of frequency component of the specific range, thereby making it possible to detect breath.

It is to be noted that it is desirable to have ability to detect bio-information at low impact with respect to human body.

Moreover, biosensors such as body motion sensor and/or breath sensor, etc. are similarly provided also with respect to a predetermined player, e.g., concert master of the orchestra 2 so that body motion and/or breath of the player are detected. It is a matter of course that those biosensors may be provided with respect to all persons of (orchestra) members constituting the orchestra to detect body motion and/or breath of respective members of the orchestra. Further, in the case where actor or actress such as singer, etc., exists, transmission of body motion, breath and/or other bio-information of that singer may be performed.

In addition, in the present invention, biosensors such acceleration pulse wave sensor, heartbeat sensor and/or breath sensor, etc. are attached with respect to a listener of a predetermined position among listeners 3, e.g., listener located at the position where listening environment is the best at the concert hall so that bio-information of the concerned listener are detected.

Figure 2:
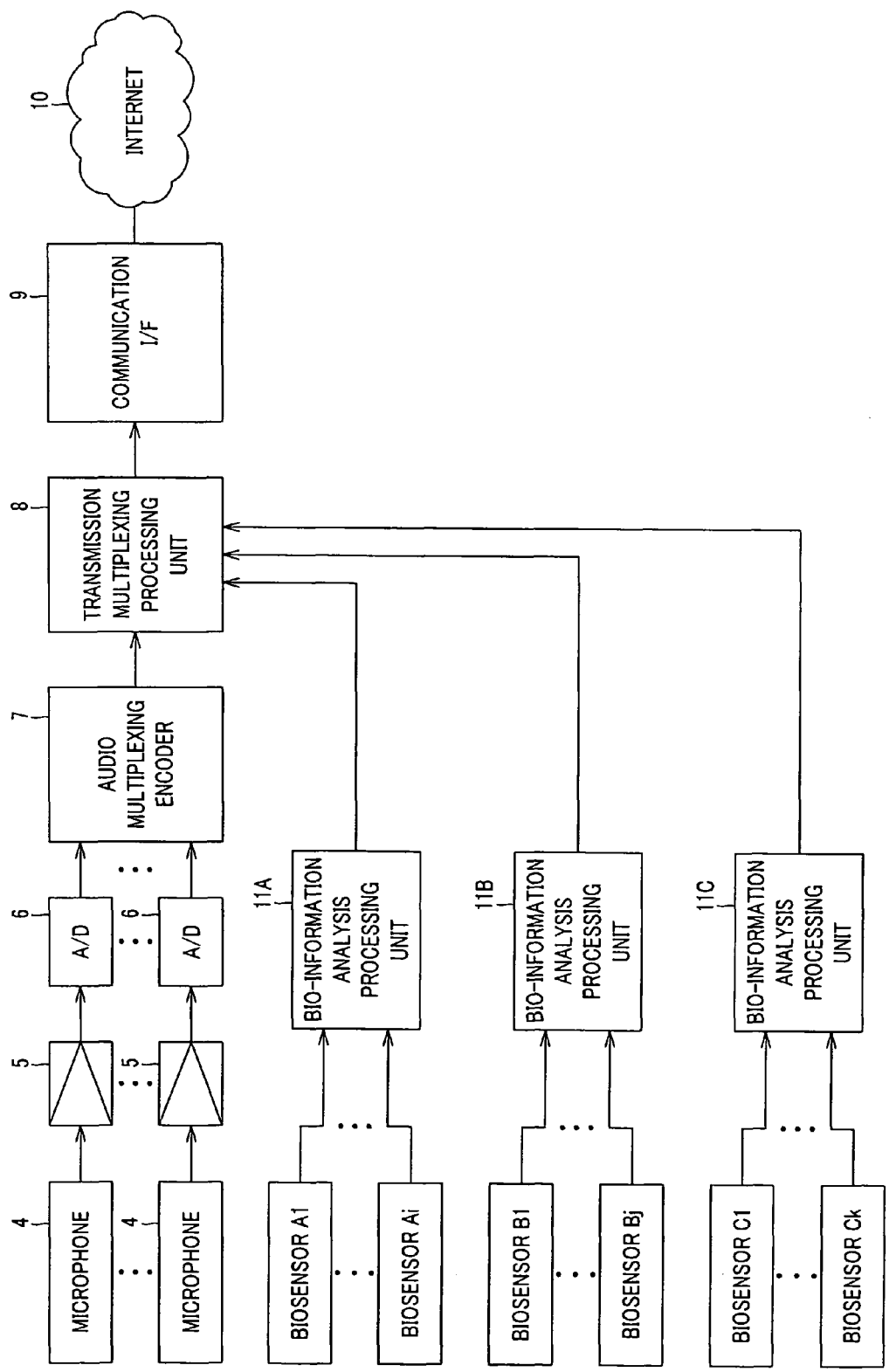
FIG. 2 is a block diagram showing the information transmission apparatus according to the present invention.

FIG. 2 is a block diagram showing a configuration example of an information transmission apparatus according to the present invention. In this example, there is employed the configuration that transmission of recorded playing music information of the orchestra is performed through Internet along with bio-information of conductor, player, actor or actress and/or listener.

Audio signals from plural microphones 4 for collecting sounds of playing music of the orchestra, i.e., audio signals of respective channels such as center channel, left channel and right channel, etc. are respectively delivered to A/D converters 6 through amplifiers 5, at which they are converted into digital audio signals.

The digital audio signals corresponding to plural channels from the plural A/D converters 6 are delivered to an audio multiplexing encoder 7, at which they are caused to undergo multiplexing-encode processing. Thereafter, the signal thus obtained is delivered to a multiplexing processing unit 8 for transmission. At the audio multiplexing encoder 7, there are included processing for compressing audio data and/or for modulating audio data for the purpose of transmission, etc.

On the other hand, in FIG. 2, biosensors A1 to Ai are sensors for acquiring bio-information of the conductor 1. Bio-information, e.g., body motion, breath and body surface temperature, etc. which have been detected at the respective biosensors A1 to Ai are delivered to a bio-information analysis processing unit 11A, at which they are analyzed. The analyzed results of the bio-information are delivered to the transmission multiplexing processing unit 8. It is to be noted that bio-information may be delivered to the transmission multiplexing processing unit 8 after undergone compression.

Moreover, biosensors B1 to Bj are sensors for acquiring bio-information of a player such as concert master, etc. in this example. Bio-information, e.g., body motion, breath and body surface temperature, etc. which have been detected at respective biosensors B1 to Bj are delivered to a bio-information analysis processing unit 11B, at which they are analyzed. The analyzed results of the bio-information are delivered to the transmission multiplexing processing unit 8.

Further, biosensors C1 to Ck are sensors for acquiring bio-information of listener located at the best listening position. Bio-information, e.g., body motion, breath and body surface temperature, etc. which have been detected at the respective biosensors C1 to Ck are delivered to a bio-information analysis processing unit 11C, at which they are analyzed. The analyzed results of the bio-information are delivered to the transmission multiplexing processing unit 8.

Figure 3A:
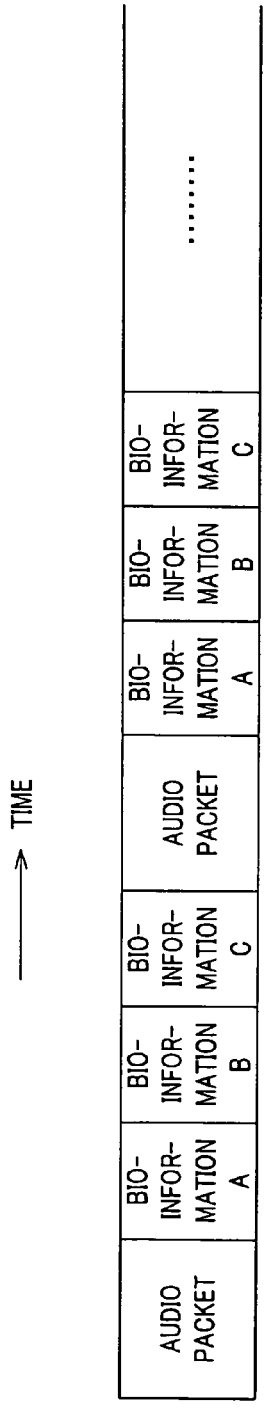
FIGS. 3A and 3B are views for explaining formats of information caused to undergo transmission by an information transmission method according to the present invention.

At the transmission multiplexing processing unit 8, audio information and bio-information are respectively packetized and multiplexed. FIG. 3A is a diagram for explaining one example of multiplexed packet data. In the case of this example, audio data are partitioned every predetermined time length and are compressed. In addition, the compressed audio data corresponding to predetermined time length are packetized. Thus, audio data packets are provided.

Moreover, analysis processing results of bio-information of conductor, player (or actor or actress) and/or listener at time period of the same predetermined time length as that of audio data from the bio-information analysis processing units 11A, 11B, 11C are respectively delivered to the transmission multiplexing processing unit 8 as bio-information A, bio-information B and bio-information C.

The transmission multiplexing processing unit 8 packetized respective bio-information A, B and C to insert the information thus packetized into areas caused to be empty in terms of time by, e.g., compression of audio signal as shown in FIG. 3A to multiplex such information thus obtained with respect to audio data packet. In this case, in this embodiment, packets of the bio-information A, the bio-information B and the bio-information C are inserted into portions after the audio data packets of corresponding predetermined time length period. Thus, transmission of the packet data thus obtained is performed in synchronism with audio data.

The audio signal and the bio-information from the transmission multiplexing processing unit 8 are sent to, e.g., communication network, Internet 10 in this example through a communication interface 9.

It is expected that in the case where transmission of the bio-information A, the bio-information B and the bio-information C is performed in synchronism with audio data in a manner as stated above, when audio data is reproduced on the real time basis at the receiving side of transmission data also as described later, processing using the bio-information A, the bio-information B and the bio-information C which have been synchronized is performed, thereby making it possible to easily reproduce the atmosphere of live performance of the concert also at the receiving side of transmission data.

It is to be noted that in the case where transmission of packets of the bio-information A, the bio-information B and the bio-information C is performed in synchronism with audio data, packets of the bio-information A, the bio-information B and the bio-information C may be inserted into portion before audio data packet of corresponding predetermined time length period.

It should be noted that in the case where transmission data is temporarily written with respect to memory or recording medium to read out such transmission data at a later time point to reproduce them in place of reproducing transmission data on the real time basis at the receiving side of transmission data, if transmission of packet of audio data and packets of the bio-information A, the bio-information B and the bio-information C is performed in such a manner that correspondence relationship between both (two kinds of) packets can be recognized, there is no necessity to synchronously perform transmission of the both (two kinds of) packets in a manner close in point of time, but, e.g., transmission of packets of the bio-information A, the bio-information B and the bio-information C with respect to respective audio data packets may be also collectively performed, e.g., at the last of audio data packet corresponding to one movement.

In this case, it is necessary that transmission of both (two kinds of) packets is performed in the state where they can be associated with each other by a method such that correspondence relation data between respective audio data packets and packets of the bio-information A, the bio-information B and the bio-information C are separately recorded, etc.

Moreover, in place of superimposing bio-information A, bio-information B and bio-information C every one packet of audio data, statistical processing of bio-information with respect to audio data corresponding to a predetermined time length serving as plural packets may be also performed at bio-information analysis processing units 11A, 11B, 11C to multiplex such statistically processed bio-information as transmission data.

Figure 3B:
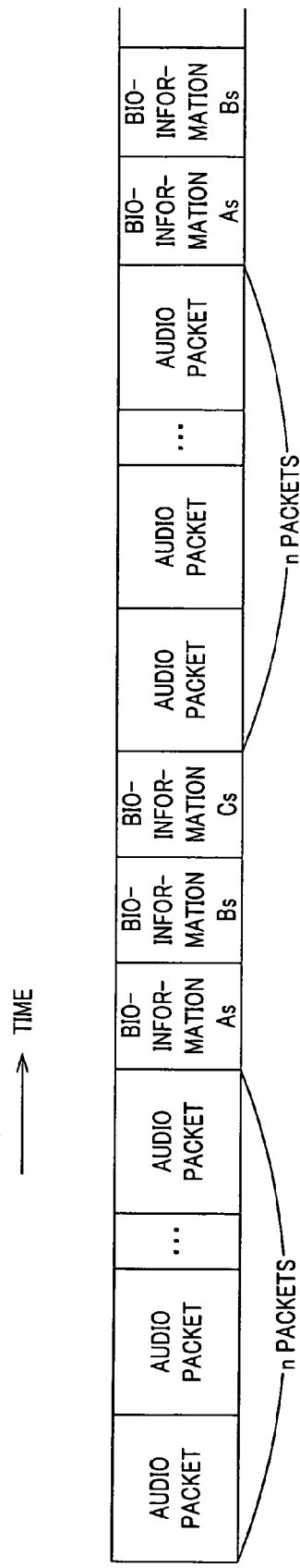

FIG. 3B is a view showing an example of transmission information in that case, and bio-information As, Bs, Cs are results obtained by performing statistical processing, e.g., averaging processing of bio-information A, B, C at time period corresponding to n number of audio data packets therebefore over the time period.

It is to be noted that while body motion and/or breath, etc. are used as bio-information in the above-described explanation, the present invention is not limited to such body motion and/or breath, but, e.g., myoelectricity, body surface temperature, sweating of skin, skin resistance, pulse, cardioelectricity and/or heartbeat, etc. may be used as bio-information acquired from conductor, player and/or actor or actress, etc.

With respect to listener considered to be placed in relatively stationary state, biochemical reaction, brain waves, magneto-encephalogram, pulse, micro-vibration and/or blood pressure, etc. may be acquired as bio-information in addition to body motion, breath, myoelectricity, body surface temperature, sweating of skin, skin resistance, pulse, cardioelectricity and/or heartbeat, etc.

As bio-information, it is unnecessary to acquire plural kinds of information as in the case of the above described example, but, e.g., only body motion, only breath or only heartbeat may be employed.

It is to be noted that while transmission of bio-information of conductor, player, actor or actress and/or listener is performed along with audio data in the above-described explanation, it is not necessarily required to all perform transmission of bio-information of three persons of conductor, player, etc. and listener, but transmission of bio-information with respect to only conductor, only player, or actor or actress, or only listener may be performed along with audio data, or transmission of arbitrary two kinds of bio-information selected from the above-mentioned three kinds of bio-information may be performed along with audio data.

The present invention is not limited to a system of performing transmission of audio data and bio-information through network such as Internet, etc. in a manner as stated above, there may be employed a system of making recording with respect to recording medium to offer the recorded data and information to user. The information recording method and the information recording apparatus of this example can be caused to be of the configuration similar to the above-described information transmission method and the information transmission apparatus except that the fact that information are recorded with respect to the recording medium is different in place of performing transmission of information.

Figure 4:
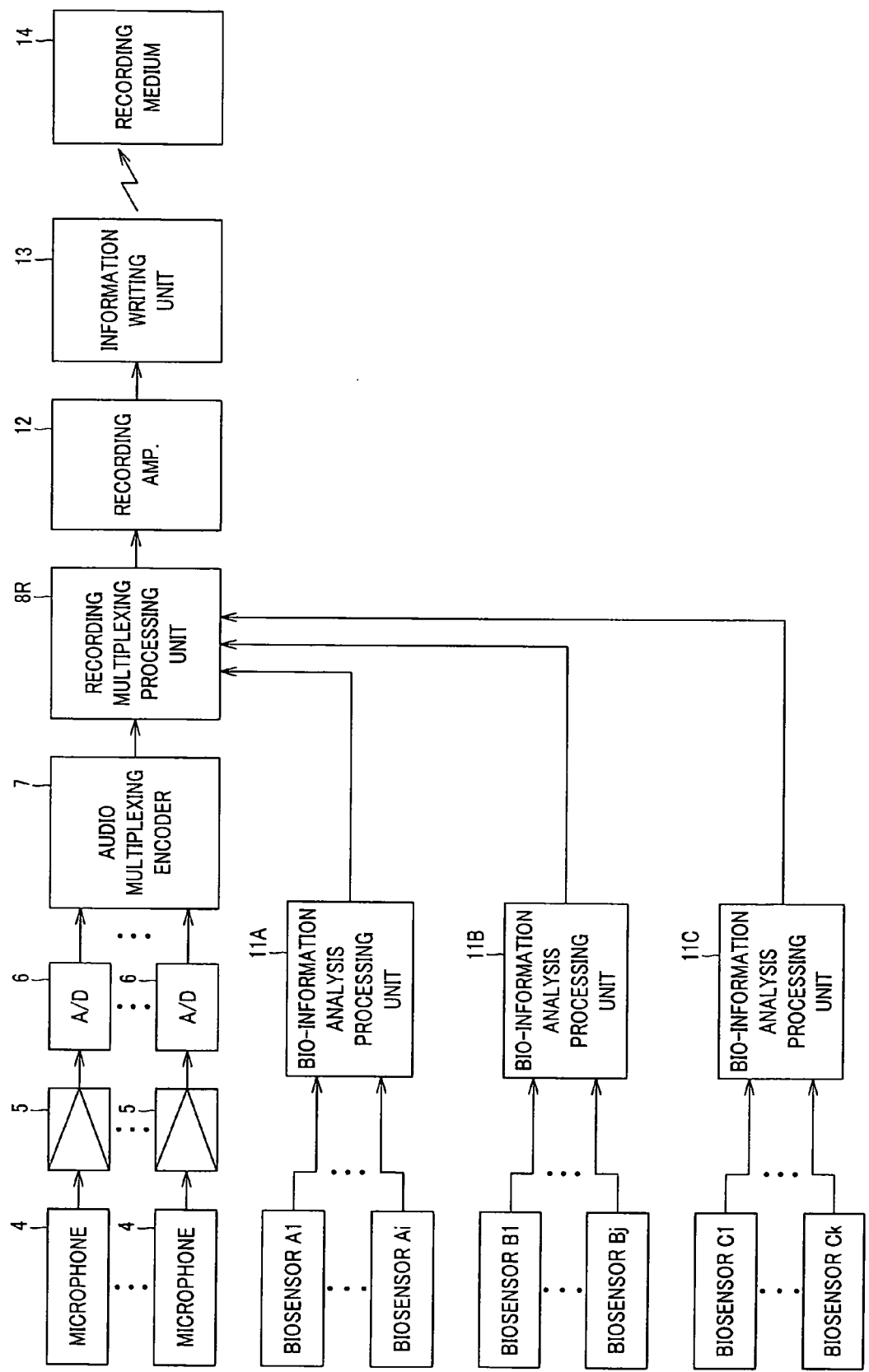
FIG. 4 is a block diagram showing an information recording apparatus according to the present invention.

FIG. 4 shows another example of the information recording apparatus according to the present invention. In the example shown in FIG. 4, the transmission multiplexing processing unit 8 is recording multiplexing processing unit 8R, but the components of the preceding stage of the multiplexing processing unit 8R are entirely the same components of the information transmission apparatus shown in FIG. 2. The recording multiplexing processing unit 8R of this example includes modulation processing for recording and/or data compression processing.

In the example shown in FIG. 4, audio data and bio-information which have been multiplexed from the recording multiplexing processing unit 8R are delivered to an information writing unit 13 through a recording amplifier 12. The information writing unit 13 writes, with respect to a recording medium 14, the audio data and the bio-information which have been multiplexed.

Here, as the recording medium 14, there may be used, e.g., optical disc such as CD-R, CD-RW, DVD, etc., magnetic tape, hard disc, IC card, and/or semiconductor memory such as card-type memory, etc.

In the case of this example, as output data of the recording multiplexing processing unit 8R, information packet stream as shown in FIG. 3 are written with respect to recording tracks or memory in the state where the output data remains to be stream thereof. In this instance, the recording area on the recording medium, or the memory area of the memory may be divided into the area for audio data and the area for bio-information to write the audio data and the bio-information in a separate manner.

In that case, when the recording medium is optical disc, the optical head is moved at a high speed onto the recording area for audio data and the recording area for bio-information to perform recording operation. When the recording medium is magnetic tape, magnetic recording head for audio data and magnetic recording head for bio-information are provided to record the audio data and the bio-information with respect to respective recording areas. Moreover, in the case where audio data and bio-information are written with respect to the memory, after audio data is written into the audio data memory area, address is changed to write bio-information into bio-information memory area.

Further, in the case where recording operation is performed onto the optical disc, or in the case where write operation is performed with respect to the memory, there may be also employed an approach such that after audio data have been all recorded, all of bio-information are written with respect to the bio-information recording area of the optical disc or the bio-information memory area of the memory.

It is to be noted that, also in both cases, information of correspondence relationship between audio data packet and corresponding bio-information packet is together recorded with respect to the recording medium or the memory. This is because it is necessary that audio data and bio-information are reproduced at the time of reproduction in the state where they are associated with each other in point of time.

Then, explanation will be given in connection with the example of the case of an information reproducing apparatus adapted for receiving multiplexed data of audio data and bio-information which have been sent to Internet to reproduce the audio data by the information transmission apparatus having the configuration as shown in FIG. 2. Several examples of information reproducing method and information reproducing apparatus exist depending upon way of utilization of bio-information at the time of reproduction.

The information reproducing method and the information reproducing apparatus are adapted to convert received bio-information into one or plural senses of visual sense, listening sense, sense of smell, sense of touch, and sense of taste to offer the sense or senses thus obtained to listener of reproduction information to thereby reproduce live atmosphere or presence of the concert.

Figure 5:
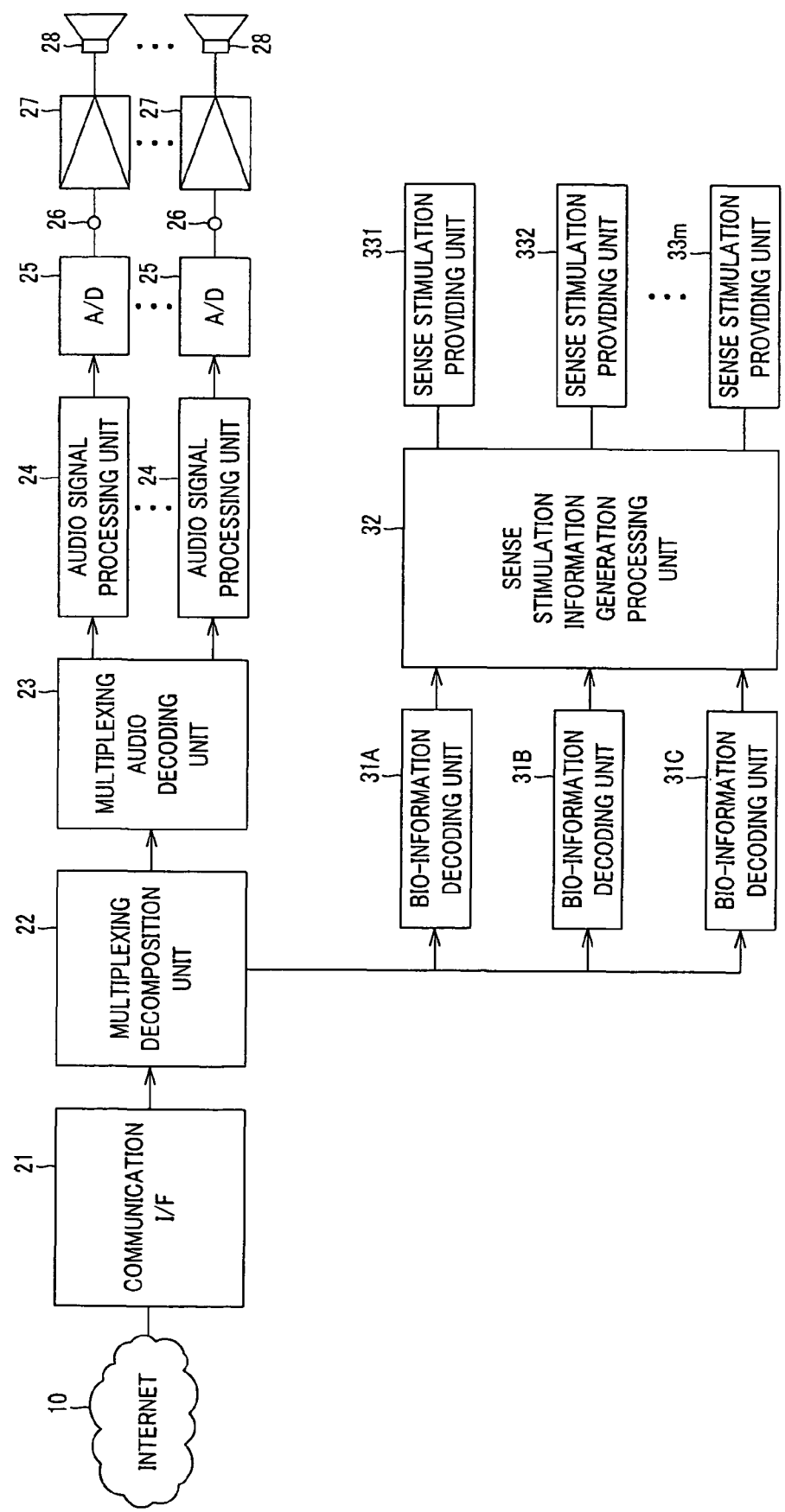
FIG. 5 is a block diagram showing an information reproducing apparatus according to the present invention.

FIG. 5 is a block diagram showing a first example of the information reproducing apparatus. As shown in FIG. 5, packets of audio data and bio-information which have been sent through an Internet 10 are delivered to a multiplexing decomposition unit 22 through a communication interface 21, at which those packets are decomposed into audio data packet and packets of bio-information A, B, C.

The audio data packet from the multiplexing decomposition unit 22 is delivered to a multiplexing audio decoding unit 23. Packet of bio-information A (bio-information of the conductor) from the multiplexing decomposition unit 22 is delivered to a bio-information decoding unit 31A, at which it is decoded. Packet of bio-information B (bio-information of player or actor (actress)) is delivered to a bio-information decoding unit 31B, at which it is decoded. Packet of bio-information C (bio-information of listener) is delivered to a bio-information decoding unit 31C, at which it is decoded. Further, the bio-information A, B, C thus decoded are delivered to a sense stimulation information generation processing unit 32.

At the multiplexing audio decoding unit 23, audio data is decoded, and is de-multiplexed into audio data of respective channels such as center channel, left channel, right channel, etc. The audio data of respective channels from the multiplexing audio decoding unit 23 are respectively delivered to D/A converters 25 through audio signal processing units 24 for respective channels, at which they are converted into analog audio signals. The analog audio signals thus obtained are sent to audio signal output terminals 26 for respective channels.

Further, audio signals of respective channels which have been sent from the analog audio signal output terminals 26 are respectively delivered to speakers 28 for respective channels through power amplifiers 27. Thus, multi-channel surround reproduction thereof is performed.

On the other hand, the sense stimulation information generation processing unit 32 generates, on the basis of bio-information A, B, C inputted thereto, sense stimulation which appeals, to five senses of listener of reproduced audio signal, biosense such as breathing, body motion or degree of excitation of the conductor, etc., biosense such as breathing, body motion or degree of excitation of player, and biosense such as degree of excitation, etc. of listener of live hall. Namely, the sense stimulation information generation processing unit 32 generates, on the basis of bio-information A, B, C inputted thereto, sense stimulation information for providing stimulations, which appeals to one of five senses or plural ones thereof of listener of reproduced audio signal.

One or plural sense stimulation providing units 331, 332, . . . 33m is or are connected to the sense stimulation information generation processing unit 32. The sense stimulation providing unit 331 is caused to be, e.g., small speaker, etc. for reproducing breath of the conductor or the player. The sense stimulation providing unit 332 is means for giving, to listener of reproduced audio signal, e.g. vibration corresponding to body motion of conductor, player or actor (or actress), or body motion of listener. The sense stimulation providing unit 332 is constituted by vibration rendering means in which in the case where, e.g., listener of reproduced audio signal sits down on a chair, the sense stimulation providing unit is attached to the chair to render (give) vibration to sitting listener.

The sense stimulation providing unit 333 may be caused to be an image display unit. The sense stimulation information generation processing unit 32 generates video information for moving image of the conductor or the player in correspondence with breath or body motion of the conductor, the player or the actor (actress), or for moving, e.g., abstracted image on the basis of bio-information of the conductor, the player, the actor (actress), or the listener in such a manner to reproduce atmosphere at that place, the degree of excitation, rhythm or tempo to deliver the video information to the sense stimulation providing unit 333. The image display unit serving as the sense stimulation providing unit 333 serves to display the above-mentioned image on the picture thereof to offer, to viewing person, as image stimulation, presence of live performance obtained from bio-information of the conductor or the player, or bio-information of listener of live hall.

In addition to the above, as the sense stimulation providing unit, there may be used a unit adapted for changing intensity of light or way of change thereof on the basis of bio-information, etc. Further, in the case of live performance of jazz or lock, there may be employed sense stimulation providing means adapted for reproducing temperature, brightness and/or sweat of that hall, or, e.g., sweat or fevered air of the player, etc.

While plural sense stimulation providing units are provided in the example shown in FIG. 5, a single sense stimulation providing unit may be provided. At the sense stimulation information generation processing unit 32, there is no necessity of using all of bio-information A of the conductor, bio-information B of the player or the actor (or actress) and bio-information C of the listener. On the basis of either one of bio-information, or combination of two bio-information, sense stimulation information may be generated.

A listener of an audio signal to be reproduced may designate, with respect to the sense stimulation information generation processing unit 32, bio-information which gives basis for generating sense stimulation as either one of bio-information of the conductor, the player or the listener, or designate, with respect thereto, such bio-information as combination of plural bio-information, whereby the sense stimulation information generation processing unit 32 generates sense stimulation on the basis of those designated bio-information.

In this case, when a listener of an audio signal to be reproduced desires to enjoy reproduction signal with a sense of the conductor, he designates bio-information of the conductor; when listener desires to enjoy listening sense at the best listening position, he designates bio-information of listener; and when listener himself desires to enjoy reproduction signal with a sense of the player, he designates bio-information of the player, thereby making it possible to enjoy desired atmosphere.

It can be expected that when all of three bio-information are designated, it becomes possible to reproduce live appeal of the concert hall.

Also previously described, there also exists the example of the case where transmission of either one of bio-information A, B, C or combination thereof is performed. In the example of the case where such transmission is performed, the sense stimulation information generation processing unit 32 is operative so that in the case where bio-information caused to undergo transmission is predetermined in advance, the sense stimulation information generation processing unit 32 serves to generate suitable sense stimulation information which has been determined in advance, or is selectively designated by user on the basis of received bio-information.

Then, another example of the information reproducing method and the information reproducing apparatus according to the present invention is adapted to perform reproduction control of received audio data on the basis of received bio-information to offer the audio data thus obtained to listener, thereby making it possible to reproduce live atmosphere or presence of the concert.

Figure 6:
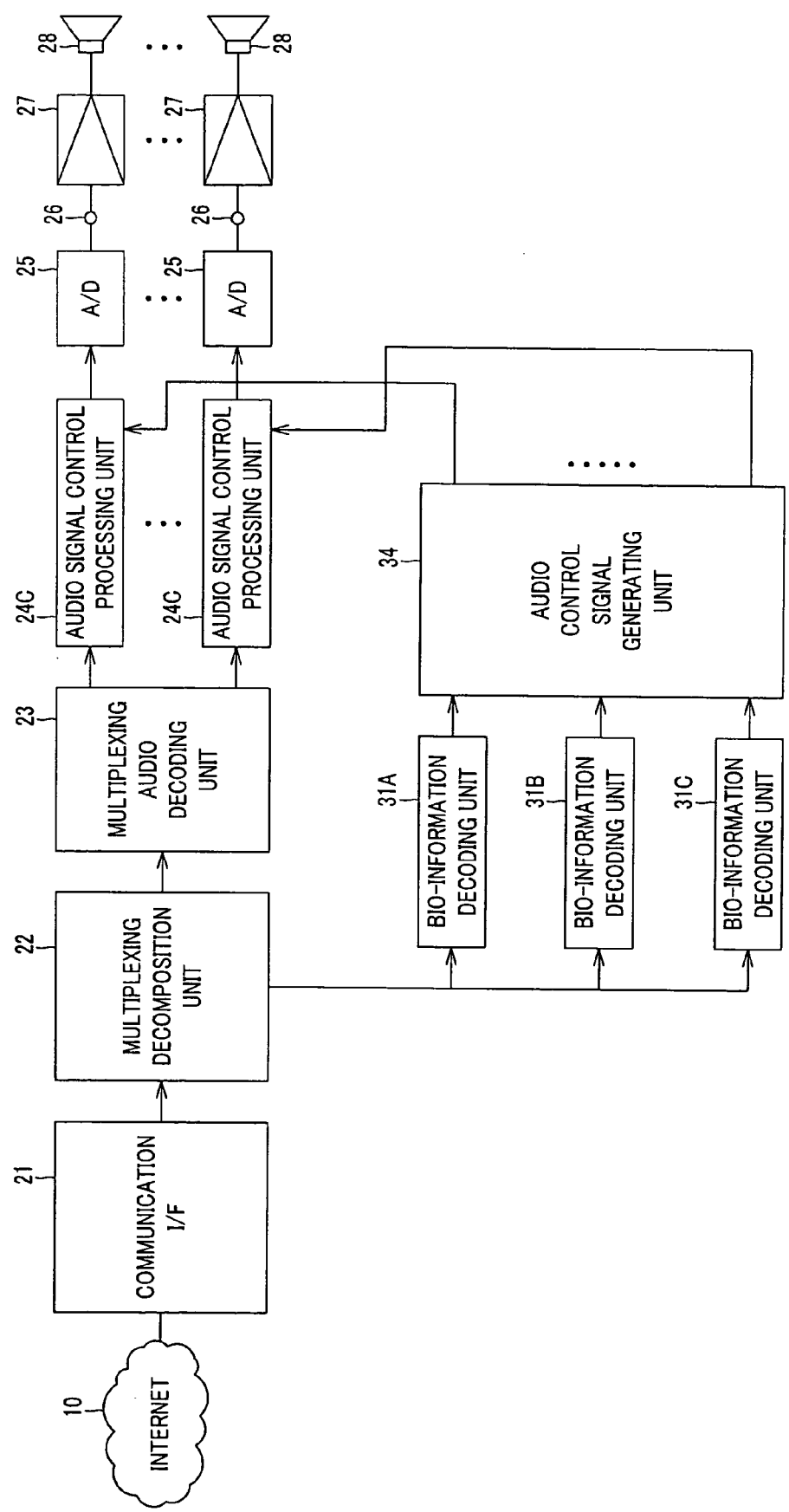
FIG. 6 is a block diagram showing another example of the information reproducing apparatus according to the present invention.

FIG. 6 is a block diagram showing another example of the information reproducing apparatus according to the present invention. With respect to the reproducing system for audio data in the information reproducing apparatus shown in FIG. 6, an audio signal control processing units 24C capable of controlling an audio signal on the basis of a control signal to be inputted are provided in place of the audio signal processing units 24 of FIG. 5.

Bio-information decoding units 31A, 31B, 31C for decoding respective bio-information A, B, C deliver decoded bio-information A, B, C to an audio control signal generating unit 34 in this example in place of the sense stimulation information generation processing unit 32 shown in FIG. 5.

The audio control signal generating unit 34 generates a control signal for audio signal on the basis of the bio-information A, B, C which have been inputted thereto. As a control signal for audio signal, there are formed control signals for controlling amplitude, phase, and/or frequency of the audio frequency, and control signals for controlling audio signal pitch and/or tempo, etc.

For example, at portions such that body motion of the conductor or the player is large, and breath thereof also greatly changes, the audio control signal generating unit 34 generates such a control signal to more emphasize change of amplitude of audio signal. At these portions, there are many cases where change of music is rapid, and/or, e.g., there takes place a change such that change into large sound volume is suddenly caused from slow and quite music. Such a control to more emphasize amplitude change of audio signal at that time is performed so that more live appeal is transmitted.

Moreover, there may be performed such a control to superimpose breath information or heartbeat information of the conductor, the player or the actor (or actress) onto an audio signal at a certain level. In this case, it can be expected that reproduction would be performed in the state where so-called "breathing" of the conductor or the player is included in music information so that live appeal having presence is included in reproduction information.

In the above-described explanation, at the audio control signal generating unit 34, there is no necessity of generating a control signal of an audio signal on the basis of all of bio-information A of the conductor, bio-information B of the player and bio-information C of the listener, but a control signal for an audio signal may be generated on the basis of either one of bio-information, or on the basis of combination of those two bio-information.

Moreover, a listener of an audio signal to be reproduced may designate bio-information serving as source for generating an audio control signal as either one of bio-information of the conductor, the player and the listener, or combination of plural bio-information thereof with respect to the audio control signal generating unit 34 to generate sense stimulation on the basis of those designated bio-information.

In this case, when a listener of an audio signal to be reproduced desires to enjoy a reproduction signal with a sense of the conductor, he designates bio-information of the conductor; when such a listener desires to enjoy listening sense at the best listening position, he designates bio-information of listener; and when such a listener himself desires to enjoy reproduction signal with a sense of the player, he designates bio-information of the player, thereby making it possible to enjoy desired atmosphere.

Further, it can be expected that all of three bio-information are designated, presence of the concert hall can be reproduced.

Also previously described, in the example of the case where transmission of either one of bio-information A, B, C is performed although the example where transmission of combination of such bio-information is performed is included, when bio-information caused to undergo transmission is determined in advance, the audio control signal generating unit 34 serves to generate a suitable audio control signal determined in advance on the basis of received bio-information.

While the above-described respective examples are directed to the example of the case where audio data and bio-information which have been caused to undergo transmission through Internet are reproduced, the example described below is directed to the example of the case where audio data and bio-information which have been written with respect to the recording memory and the memory are reproduced.

In this example, other components are entirely the same as the previously described components of FIGS. 5 and 6 except that the portion of the previously described communication interface 21 in the examples of FIGS. 5 and 6 is replaced by information read-out unit for reading out audio data and/or bio-information from the recording medium or the memory, and reproduction amplifier.

Figure 7:
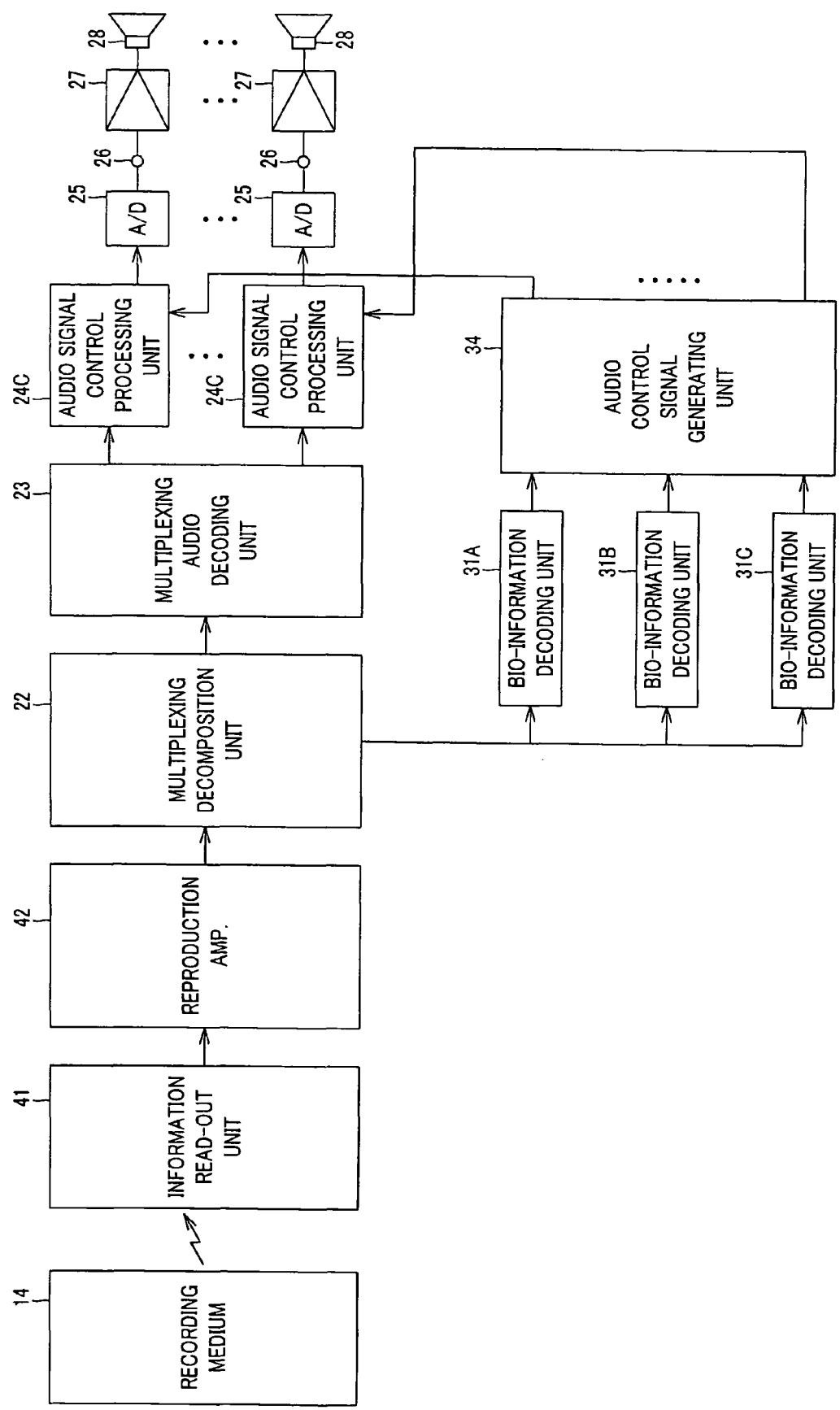
FIG. 7 is a block diagram showing a further example of the information reproducing apparatus according to the present invention.

FIG. 7 shows another configuration example of an information reproducing apparatus corresponding to the information reproducing apparatus shown in FIG. 6. This example is directed to the example of the case where information is read out from recording medium 14, wherein audio information and bio-information are read out from the recording medium 14 by an information read-out unit 41, and the information which has been read out is delivered to multiplexing decomposition unit 22 through a reproduction amplifier 42. The components of the succeeding stage of the multiplexing decomposition unit 22 are entirely the same as those of the case of FIG. 6.

In the case where the information reproducing apparatus shown in FIG. 7 is applied to the above-described information reproducing apparatus shown in FIG. 5, components of the succeeding stage of the multiplexing decomposition unit 22 are entirely the same as those shown in FIG. 5.

Further, the operations and the effects in the case of the apparatus shown in FIG. 7 are respectively entirely the same as those of the above-described apparatus shown in FIGS. 5 and 6.

It is to be noted that in the case where audio data and bio-information are respectively written in recording areas or memory areas which are respectively separated of the recording medium or the memory when reproduction is performed from the recording medium in the apparatus shown in FIG. 7, multiplexing decomposition unit 22 is not provided at the information reproducing apparatus, but the information read-out unit 41 serves to distribute audio data and bio-information to multiplexing audio decoding unit 23 and bio-information decoding units 31A, 31B, 31C depending upon whether or not data or information to be read out is audio data or bio-information.

Further, in the case where the recording medium is magnetic tape, and audio data and bio-information are recorded with respect to separate tracks, the information reproducing apparatus is caused to be of the configuration in which head for reproducing audio data and head for reproducing bio-information are provided, and signal processing systems such as read-out unit and/or decoding unit, etc. which are adapted for reproducing respective information are respectively provided at the succeeding stage of the respective reproduction heads.

While the case where only audio information is subject to transmission, recording and/or reproduction has been explained in the above-described explanation, information subject to transmission, recording, reproduction may be only information of image, or may be combination of audio information and information of image. For example, the case of live broadcast of play or drama played at theater, or live recording are examples thereof. In that case, transmission of bio-information of player and/or bio-information of a person who performs playgoing is performed along with video information, or such bio-information are recorded along with video information.

While the present invention is applied to the case of Internet live broadcast or live recording in the above-described respective examples, there may be also employed such an approach to extract bio-information of conductor, player and/or actor (actress) from audio information and/or video information recorded in advance on recording medium, or stored in advance in memory to multiplex those bio-information with respect to audio information and/or video information to perform transmission thereof.

This is applied to the case where Internet broadcast of audio information and/or video information which have been read out from, e.g., recorded recording medium or memory is performed, or audio information and/or video information which have been read out from recoded recording medium or memory are recorded onto recording medium, or are written into memory.

Figure 8:
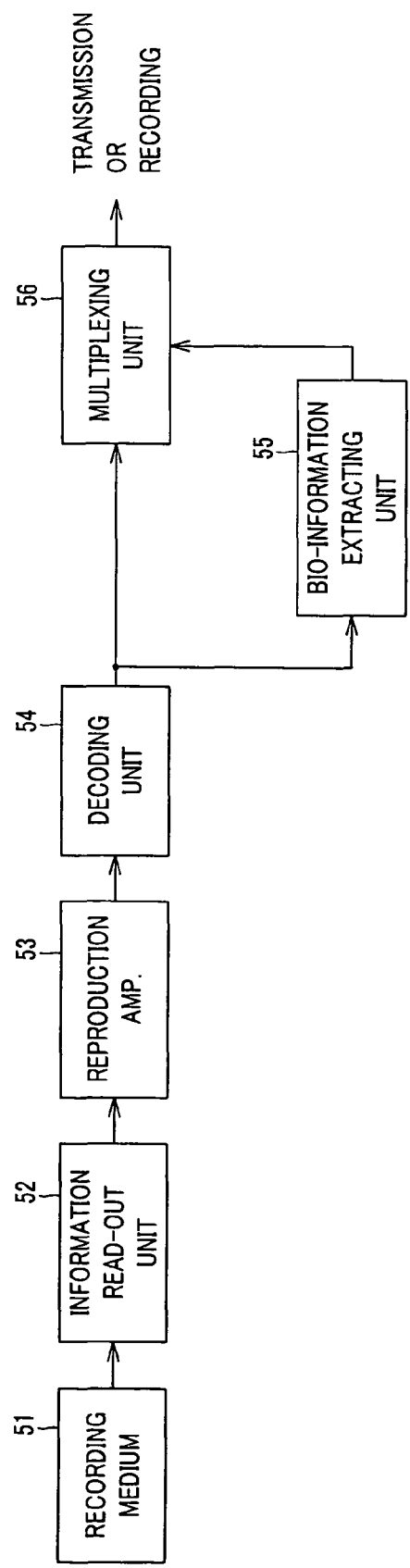
FIG. 8 is a block diagram showing another example of the information transmission apparatus according to the present invention.

FIG. 8 is a block diagram showing the configuration of the essential part of the information transmission apparatus or the information recording apparatus in that case. Namely, audio data and/or video data which have been read out from a recording medium 51 by an information read-out unit 52 are delivered to a decoding unit 54 through a reproduction amplifier 53, at which they are decoded.

Further, audio data and/or video data which have been decoded are delivered to a multiplexing unit 56, and are delivered to a bio-information extracting unit 55. The bio-information extracting unit 55 serves to extract, from audio data and/or video data, bio-information such as breath and/or body motion, etc. of player or performer such as singer or actor (actress), etc. to deliver the bio-information thus extracted to the multiplexing unit 56.

The multiplexing unit 56 serves to multiplex the bio-information from the bio-information extracting unit 55 with respect to the audio data and/or the video data from the decoding unit 54. Further, transmission of the multiplexed information thus obtained is performed through network, or such multiplexed information is recorded onto recording medium.

It is to be noted that there may be employed such an approach to control an audio signal or a video signal which has been reproduced on the basis of bio-information from the bio-information extracting unit 55 similarly to the example of FIG. 7 in place of performing transmission or recording.

While, in the above-described explanation, transmission of transmission data such as audio data and/or video data, and bio-information, etc. is performed in the state where they are packetized, it is not indispensable to packetize transmission data. Transmission of audio data and/or video data and bioinformation is performed in the state where their frequency bands are caused to be different from each other, or such data and information may be recorded in the same state as above.

In addition, while the above-described example is directed to the case of Internet live broadcast, etc., it is a matter of course that the present invention is not limited to such transmission method.

It is to be noted that while the present invention has been described in accordance with certain preferred embodiments thereof illustrated in the accompanying drawings and described in detail, it should be understood by those ordinarily skilled in the art that the invention is not limited to embodiments, but various modifications, alternative constructions or equivalents can be implemented without departing from the scope and spirit of the present invention as set forth by appended claims.

INDUSTRIAL APPLICABILITY

As described above, in accordance with the present invention, bio-information of conductor, player, actor (actress), listener or playgoing person is caused to undergo transmission, or is recorded in combination along with audio information and video information, thereby making it possible to reproduce the atmosphere of concert hall or live hall by using such bio-information at the side where these information are reproduced.

The invention claimed is:

1. An information transmission method, comprising:
   acquiring one or more of audio information and video information of a music performance at a given location;
   detecting, concurrent with the acquiring of the one or more of audio information and video information of the music performance, body motion information indicative of a tempo of music of the music performance and bio-information of at least one individual present at the given location;
   partitioning the acquired one or more of audio information and video information of the music performance into lengths of partitioned data each of which corresponds to a predefined time interval;
   compressing and packetizing the lengths of partitioned data into a stream of first data packets having empty regions resulting from the compression of the lengths of the partitioned data;
   performing statistical processing of the body motion information indicative of the tempo of the music of the music performance and bio-information over predetermined time intervals corresponding to respective pluralities of the first data packets of the one or more of audio information and video information;
   packetizing the statistically processed body motion information indicative of the tempo of the music of the music performance and bio-information into respective pluralities of second data packets corresponding to the respective pluralities of the first data packets;
   multiplexing the stream of first data packets with the second data packets by inserting a respective plurality of second data packets, which corresponds to one of the predetermined time intervals, into one of the empty regions of the stream that is adjacent to a respective plurality of first data pockets which corresponds to a same one of the predetermined time intervals; and
   transmitting the multiplexed stream.

2. The information transmission method as set forth in claim 1, wherein the at least one individual includes a speaker, a player, an actor, an actress, or a conductor who serves as a source of the audio information, and/or a performer of a photographed person who is included within the video information.

3. The information transmission method as set for in claim 1, wherein the at least one individual includes a listener who is present at the given location when the audio information is acquired and/or a viewer present at the given location when the video information is acquired.

4. The information transmission method as set forth in claim 1, wherein the bio-information selected from the group consisting of myoelectricity, body surface temperature, skin sweating, skin pressure, pulse, breath, micro-vibration, cardioelectricity, heartbeat, and blood pressure.

5. The information transmission method as set forth in claim 1, wherein the detected body motion information indicative of the tempo of the music of the music performance and bio-information is extracted from the one or more of audio information and video information of the music performance, 6. An information transmission apparatus, comprising:
   information acquiring means for acquiring one or more of audio information and video information of a music performance at a given location;
   detecting means for detecting, concurrent with the acquiring of the one or more of audio information and video information of the music performance, body motion information indicative of a tempo of music of the music performance and bio-information of at least one individual present at the given location; and
   first packetizing means for partitioning the acquired one or more of audio information and video information of the music performance into lengths of partitioned data each of which corresponds to a predefined time interval, and for compressing and packetizing the lengths or partitioned data into a stream of first data packets having empty regions resulting from the compression of the partitioned data;
   analysis means for performing statistical processing of the body motion information indicative of the tempo of the music of the music performance and bio-information over predetermined time intervals corresponding to respective pluralities of the first data packets of the one or more of audio information and video information;
   second packetizing means for packetizing the statistically processed body motion information indicative of the tempo of the music of the music performance and bio-information into respective pluralities of second data packets corresponding to the respective pluralities of the first data packets;
   multiplexing means for multiplexing the stream of first data packets with the second data packets by inserting a respective plurality of second data packets, which corresponds to one of the predetermined time intervals, into one of the empty regions of the stream that is adjacent to a respective plurality of first data packets which corresponds to a same one of the predetermined time intervals; and
   transmission means for transmitting the multiplexed stream.

7. The information transmission apparatus as set forth in claim 6, wherein the at least one individual includes a speaker, a player, an actor, or a conductor who serves as a source of the audio information, and/or a performer or a photographed person who is included within the video information.

8. The information transmission apparatus as set forth in claim 6, wherein the at least one individual includes a listener who is present at the given location when the audio information is acquired and/or a viewer present at the given location when the video information is acquired.

9. The information transmission apparatus as set forth in claim 6, wherein the bio-information is selected from the group consisting of myoelectricity, body surface temperature, skin sweating, skin resistance, pulse, breath, micro-vibration, cardioelectricity, heartbeat, and blood pressure.

10. The information transmission apparatus as set forth in claim 6, wherein the detecting means extracts the detected body motion information indicative of the tempo of the music of the music performance and bio-information from the one or more of audio information and video information of the music performance.

11. An information recording method, comprising:
acquiring one or more of audio information and video information of a music performance at a given location;
detecting, concurrent with the acquiring of the one or more of audio information and video information of the music performance, body motion information indicative of a tempo of music of the music performance and bio-information of at least one individual present at the given location;
partitioning packetizing the acquired one or more of audio information and video information of the music performance into lengths of partitioned data each of which corresponds to a predefined time interval;
compressing and packetizing the lengths of partitioned data into a stream of first data packets having empty regions resulting from the compression of the partitioned data;
performing statistical processing of the body motion information indicative of the tempo of the music of the music performance and bio-information over predetermined time interval corresponding to respective pluralities of first data packets of one or more of audio information and video information;
packetizing the statistically processed body motion information indicative of the tempo of the music of the music performance and bio-information into respective pluralities of second data packets corresponding to the respective pluralities of the first data packets;
multiplexing the stream of first data packets with the second data packets by inserting a respective plurality of second data packets, which corresponds to one of the predetermined time intervals, into one of the empty regions of the stream that adjacent to a respective plurality of first data packets which corresponds to a same one of the predetermined time intervals; and
recording the multiplexed stream onto a predetermined recording medium.

12. The information recording method as set forth in claim 11, wherein the at least one individual includes a speaker, a player, an actor, or a conductor who serves a source of the audio information, and/or a performer or a photographed person who is included within the video information.

13. The information recording method as set forth in claim 11, wherein the at least one individual includes a listener who is present at the given location when the audio information is acquired and/or a viewer present at the given location when the video information is acquired.

14. The information recording method as set forth in claim 11, wherein the bio-information is selected from the group consisting of myoelectricity, body surface temperature, skin sweating, skin resistance, pulse, breath, micro-vibration, cardioelectricity, heartbeat, and blood pressure.

15. The information recording method as set forth in claim 11, wherein the detected the recording medium is at least one of optical disc, magnetic tape, hard disc and semiconductor memory.

16. The information recording method as set forth in claim 11, wherein the body motion information indicative of the tempo of the music of the music performance and bio-information is extracted from the one or more of audio information and video information of the music performance.

17. An information recording apparatus, comprising:
information acquiring means, for acquiring one or more of audio information and video information of a music performance at a given location;
detecting means for detecting, concurrent with the acquiring of the one or more of audio information and video information of the music performance, body motion information indicative of a tempo of music of the music performance and bio-information of at least one individual present at the given location; and
first packetizing means for partitioning the acquired one or more of audio information and video information of the music performance into lengths of partitioned data each of which corresponds to a predefined time interval, and for compressing and packetizing the lengths of partitioned data into a stream of first data packets having empty regions resulting from the compression of the partitioned data;
analysis means for performing statistical processing of the body motion information indicative of the tempo of the music of the music performance and bio-information over predetermined time intervals corresponding to respective pluralities of the first data packets of the one or more of audio information and video information;
second packetizing means for packetizing the statistically processed body motion information indicative of the tempo of the music of the music performance and bio-information into respective pluralities of second date packets corresponding to the respective pluralities of the first data packets;
multiplexing means for multiplexing the stream of first data packets with the second data packets by inserting a respective plurality of second data packets, which corresponds to one of the predetermined time intervals, into one of the empty regions of the stream that is adjacent to a respective plurality of first data packets which corresponds to a same one of the predetermined time intervals; and
recording means for recording the multiplexed stream onto a predetermined recording medium.

18. The information recording apparatus as set forth in claim 17, wherein the at least one individual includes a speaker, a player, an actor, or a conductor who serves as a source of the audio information, and/or a performer or a photographed person who is included within the video information.

19. The information recording apparatus as set forth in claim 17, wherein the at least one individual includes a listener who is present at the given location when the audio information is acquired and/or a viewer present at the given location when the video information is acquired.

20. The information recording apparatus as set forth in claim 17, wherein the bio-information is selected from the group consisting of myoelectricity, body surface temperature, skin sweating, skin resistance, pulse, breath, micro-vibration, cardioelectricity, heartbeat, and blood pressure.

21. The information recording apparatus as set forth in claim 17, wherein the recording medium is selected from the group consisting of optical disc, magnetic tape, hard disc, and semiconductor memory.

22. The information recording apparatus as set forth in claim 17, wherein the detecting means extracts the detected body motion information indicative of the tempo of the music of the music performance and bio-information from the one or more of audio information and video information.

23. An information reproducing method, comprising:
acquiring one or more of audio information and video information of a music performance at a given location;
detecting, concurrent with the acquiring of the one or more of audio information and video information of the music performance, body motion information indicative of a tempo of music of the music performance and bio-information of at least one individual present at the given location;
partitioning the acquired one or more of audio information and video information of the music performance into lengths of partitioned data each of which corresponds to a predefined time interval;
compressing and packetizing the lengths of partitioned data into a stream of first data packets having empty regions resulting from the compression of the lengths of the partitioned data;
performing statistical processing of the body motion information indicative of the tempo of the music of the music performance and bio-information over predetermined time intervals corresponding to respective pluralities of the first data packets of the one or more of audio information and video information;
packetizing the statistically processed body motion information indicative of the tempo of the music of the music performance and bio-information into respective pluralities of second data packets corresponding to the respective pluralities of the first data packets;
multiplexing the stream of first data packets with the second data by inserting a respective plurality of second data packets, which corresponds to one of the predetermined time intervals, into one of the empty regions of the stream that is adjacent to a respective plurality of first data packets which corresponds to a same one of the predetermined time intervals;
decomposing a multiplexed data stream into respective pluralities of first data packets at one or more of audio information and video information of a music performance and into corresponding respective pluralities of second data packets of statistically processed body motion information indicative of a tempo of music of the music performance and bio-information, the multiplexed data stream having each respective plurality of second data packets of the statistically processed body motion information indicative of the tempo of the music of the music performance and bio-information which corresponds to a given predetermined time interval being disposed adjacent to a respective plurality of first data packets which corresponds to a same predetermined time interval in regions of the data stream resulting from partitioning acquired one or more of audio information and video information into lengths of partitioned data each corresponding to a predefined time interval and compressing the lengths of partitioned data, the acquired one or more of audio information and video information of the music performance being acquired at a performance at a given location, the body motion information indicative of the tempo of the music of the music performance and bio-information being of at least one individual present at the given location and being detected concurrent with the acquiring of the one or more of audio information and video information, the statistically processed body motion information indicative of the tempo of the music of the music performance and bio-information being generated by performing statistical processing of the detected body motion information indicative of the tempo of the music of the music performance and bio-information over predetermined time intervals corresponding to respective pluralities of the first data packets;
reproducing the one or more of audio information and video information for delivery to a user;
providing, to the user, sense stimulation based on the body motion information indicative of the tempo of the music of the music performance and bio-information concurrent with the delivery of the one or more of the audio information and video information of the music performance; and
generating video information for a moving image in correspondence with the body motion information indicative of the tempo of the music of the music performance.

24. The information reproducing method as set forth in claim 23, wherein the multiplexed data stream is received through a transmission method.

25. The information reproducing method as set forth in claim 23, wherein the multiplexed data stream is read out from a recording medium.

26. The information reproducing method as set forth in claim 23, wherein the at least one individual includes a speaker, a player, an actor, or a conductor who serves as a source of the audio information, and/or a performer or a photographed person who is included within the video information.

27. The information reproducing method as set forth in claim 23, wherein the at least one individual includes a listener present at the given location when the audio information is acquired and/or a viewer present at the given location when the video information is acquired.

28. An information reproducing method, comprising:
acquiring one or more of audio information and video information of a music performance at a given location;
detecting, concurrent with the acquiring of the one or more of audio information and video information of the music performance, body motion information indicative of a tempo of music of the music performance and bio-information of at least one individual present at the given location;
partitioning the acquired one or more of audio information and video information of the music performance into lengths of partitioned data each of which corresponds to a predefined time interval;
compressing and packetizing the lengths of partitioned data into a stream of first data packets having empty regions resulting from the compression of the lengths of the partitioned data;
performing statistical processing of the body motion information indicative of the tempo of the music of the music performance and bio-information over predetermined time intervals corresponding to respective pluralities of the first data packets of the one or more of audio information and video information;
packetizing the statistically processed body motion information indicative of the tempo of the music of the music performance and bio-information into respective pluralities of second data packets corresponding to the respective pluralities of the first data packets;

multiplexing the stream of first data packets with the second data packets by inserting a respective plurality of second data packets, which corresponds to one of the predetermined time intervals, into one of the empty regions of the stream that is adjacent to a respective plurality of first data packets which corresponds to a same one of the predetermined time intervals;

decomposing a multiplexed data stream into respective pluralities of first data packets of one or more of audio information and video information of a music performance and into corresponding respective pluralities of second data packets of statistically processed body motion information indicative of a tempo of music of the music performance and bio-information, the multiplexed data stream having each respective plurality of second data packets of the statistically processed body motion information indicative of the tempo of the music of the music performance and bio-information which corresponds to a given predetermined time interval being disposed adjacent to a respective plurality of first data packets which corresponds to a same predetermined time interval in regions of the data stream resulting from partitioning acquired one or more at audio information and video information of the music performance into lengths of partitioned data each corresponding to a predefined time interval and compressing the lengths of partitioned data, the acquired one or more of audio information and video information being acquired at a performance at a given location, the body motion information indicative of the tempo of the music of the music performance and bio-information being of at least one individual present at the given location and being detected concurrent with the acquiring of the one or more of audio information and video information, the statistically processed body motion information indicative of the tempo of the music of the music performance and bio-information being generated by performing statistical processing of the detected body motion information indicative of the tempo of the music of the music performance and bio-information over predetermined time intervals corresponding to respective pluralities of the first data packets;

controlling, based on the body motion information indicative of the tempo of the music of the music performance and bio-information, reproduction of the one or more of audio information and video information of the music performance; and generating video information for a moving image in correspondence with the body motion information indicative of the tempo of the music of the music performance.

29. The information reproducing method a set forth in claim 28, wherein the multiplexed data stream is are received through a transmission medium.

30. The information reproducing method as set forth in claim 28, wherein the multiplexed data stream is read out from a record medium.

31. The information reproducing method as set forth in claim 28, wherein the at least one individual includes a speaker, a player, an actor, or a conductor who serves as a source of the audio information, and/or a performer or a photographed person who is included within the video information.

32. The information reproducing method as set forth in claim 28, wherein the at least one individual includes a listener present at the given location when the audio information is acquired and/or a viewer present at the given location when the video information is acquired.

33. A system, comprising:
an information processing apparatus, including:
information acquiring means for acquiring one or more of audio information and video information of a music performance at a given location,
detecting means for detecting, concurrent with the acquiring or the one or more of audio information and video information of the music performance, body motion information indicative of a tempo of music of the music performance and bio-information of at least one individual present at the given location, and
first packetizing means for partitioning the acquired one or more of audio information and video information of the music performance into lengths of partitioned data each of which corresponds to a predefined time interval, and for compressing and packetizing the lengths of partitioned data into a stream of first data packets having empty regions resulting from the compression of the partitioned data,
analysis means for performing statistical processing of the body motion information indicative of the tempo of the music of the music performance and bio-information over predetermined time intervals corresponding to respective pluralities of the first data packets of the one or more of audio information and video information,
second packetizing means for packetizing the statistically processed body motion information indicative of the tempo of the music of the music performance and bio-information into respective pluralities second data packets corresponding to the respective pluralities of the first data packets, and
multiplexing means for multiplexing the stream of first data packets with the second data packets by inserting a respective plurality of second data packets, which corresponds to one of the predetermined time intervals, into one of the empty regions of the stream that is adjacent to a respective plurality of first data packets which corresponds to a same one of the predetermined time intervals;
an information reproducing apparatus, including;
means for decomposing the multiplexed data stream into respective pluralities of first data packets of one or more of audio information and video information of a music performance and into corresponding respective pluralities of second data packets of statistically processed body motion information indicative of a tempo of music of the music performance and bio-information, the multiplexed data stream having each respective plurality of second data packets of the statistically processed body motion information indicative of the tempo of the music of the music performance and bio-information which corresponds to a given predetermined time interval being disposed adjacent to a respective plurality of first data packets which corresponds to a same predetermined time interval in regions of the data stream resulting from partitioning acquired one or more of audio information and video information into lengths of partitioned data each corresponding to a predefined time interval and compressing the lengths of partitioned data, the acquired one or more of audio information and video information of the music performance being acquired at a performance at a given location, the body motion information indicative of the tempo of the music of the music performance and bio-information being of at least one individual present at the given location and being detected concurrent with the acquiring or the one or more of audio information and video information, the statistically processed body motion information indicative of the tempo of the music of the music performance and bio-information being generated by performing statistical processing of the detected body motion information indicative of the tempo of the music of the music performance and bio-information over predetermined time intervals corresponding to respective pluralities of the first data packets, means for reproducing the one or more of audio information and video information of the music performance for delivery to a user, means for providing, to the user, sense stimulation based on the body motion information indicative of the tempo of the music of the music performance and bio-information concurrent with the delivery of the one or more of the audio information and video information of the music performance, and means for generating video information for a moving image in correspondence with the body motion information indicative of the tempo of the music of the music performance, 34. The information reproducing apparatus as set forth in claim 33, further comprising: means for receiving the multiplexed data stream through a transmission medium.

35. The information reproducing apparatus as set forth in claim 33, further comprising: means for reading out the multiplexed data stream from a recording medium.

36. The information reproducing apparatus as set forth in claim 33, wherein the at least one individual includes a speaker, a player, an actor, or a conductor who serves as a source of the audio information, and/or a performer or a photographed person who is included within the video information.

37. The information reproducing apparatus as set forth in claim 33, wherein the at least one individual includes a listener present at the given location when the audio information is acquired and/or a viewer present at the given location when the video information is acquired.

38. A system, comprising:
an information processing apparatus, including:
information acquiring means for acquiring one or more of audio information and video information of a music performance at a given location,
detecting means for detecting, concurrent with the acquiring of the one or more of audio information and video information of the music performance, body motion information indicative of a tempo of music of the music performance and bio-information of at least one individual present at the given location, and
first packetizing means for partitioning the acquired one or more of audio information and video information of the music performance into lengths of partitioned data each of which corresponds to a predefined time interval, and for compressing and packetizing the lengths of partitioned data into a stream of first data packets having empty regions resulting from the compression of the partitioned data,
analysis means for performing statistical processing of the body motion information indicative of the tempo of the music of the music performance and bio-information over predetermined time intervals corresponding to respective pluralities of the first data packets of the one or more of audio information and video information,
second packetizing means for packetizing the statistically processed body motion information indicative of the tempo of the music of the music performance bio-information into respective pluralities of second data packets corresponding to the respective pluralities of the first data packets, and
multiplexing means for multiplexing the stream of first data packets with the second data packets by inserting a respective plurality of second data packets, which corresponds to one of the predetermined time intervals, into one of the empty regions of the stream that is adjacent to a respective plurality of first data packets which corresponds to a same one of the predetermined time intervals;
an information reproducing apparatus, including:
means for decomposing the multiplexed data stream into respective pluralities of first data packets of one or more of audio information and video information of a music performance and into corresponding respective pluralities of second data packets of statistically processed body motion information indicative of a tempo of music of the music performance and bio-information, the multiplexed data stream having each respective plurality of second data packets of the statistically processed body motion information indicative of the tempo of the music of the music performance and bio-information which corresponds to a given predetermined time interval being disposed adjacent to a respective plurality of first data packets which corresponds to a same predetermined time interval in regions of the data stream resulting from partitioning acquired one or more of audio information and video information of the music performance into lengths of partitioned data each corresponding to a predefined time interval and compressing the lengths of partitioned data, the acquired one or more of audio information and video information of the music performance being acquired at a performance at a given location, the body motion information indicative of the tempo of the music of the music performance and bio-information being of at least one individual present at the given location and being detected concurrent with the acquiring of the one or more of audio information and video information of the music performance, the statistically processed body motion information indicative of the tempo of the music of the music performance and bio-information being generated by performing statistical processing of the detected body motion information indicative of the tempo of the music of the music performance and bio-information over predetermined time intervals corresponding to respective pluralities of the first data packets,
means for controlling, based on the body motion information indicative of the tempo of the music of the music performance and bio-information, reproduction of the one or more of audio information and video information of the music performance, and
means for generating video information for a moving image in correspondence with the body motion information indicative of the tempo of the music of the music performance.

39. The information reproducing apparatus as set forth in claim 38, further comprising: means for receiving the multiplexed data stream through a transmission medium.

40. The information reproducing apparatus as set forth in claim 38, further comprising: means for reading out the multiplexed data stream from a recording medium.

41. The information reproducing apparatus as set forth in claim 38, wherein the at least one individual includes a speaker, a player, an actor, or a conductor who serves as a source of the audio information, and/or a performer or a photographed person who is included within the video information.

42. The information reproducing apparatus as set forth in claim 38, wherein the at least one individual includes a listener present at the given location when the audio information is acquired and/or a viewer present at the given location when the video information is acquired.

43. A system, comprising:
an information recording apparatus, comprising:
information acquiring means for acquiring one or more of audio information and video information of a music performance at a given location,
detecting means for detecting, concurrent with the acquiring of the one or more of audio information and video information of the music performance, body motion information indicative of a tempo of music of the music performance and bio-information of at least one individual present at the given location,
first packetizing means for partitioning the acquired one or more of audio information and video information of the music performance into lengths of partitioned data each of which corresponds to a predefined time interval, and for compressing and packetizing the lengths of partitioned data into a stream of first data packets having empty regions resulting from the compression of the partitioned data,
analysis means for performing statistical processing of the body motion information indicative of the tempo of the music of the music performance and bio-information over predetermined time intervals corresponding to respective pluralities of the first data packets of the one or more of audio information and video information,
second packetizing means for packetizing the statistically processed body motion information indicative of the tempo of the music of the music performance and bio-information into respective pluralities of second data packets corresponding to the respective pluralities of the first data packets,
multiplexing means for multiplexing the stream of first data packets with the second data packets by inserting a respective plurality of second data packets, which corresponds to one of the predetermined time intervals, into one of the empty regions of the stream that is adjacent to a respective plurality of first data packets which corresponds to a same one of the predetermined time intervals, and
recording means for recording the multiplexed stream onto a predetermined recording medium; and
a non-transitory recording medium having recorded therein the multiplexed data stream comprised of respective pluralities of first data packets of one or more of audio information and video information of a music performance and corresponding respective pluralities of second data packets of statistically processed body motion information indicative of a tempo of music of the music performance and bio-information, the multiplexed data stream having each respective plurality of second data packets of the statistically processed body motion information indicative of the tempo of the music of the music performance and bio-information which corresponds to a given predetermined time interval being disposed adjacent to a respective plurality of first data packets which corresponds to a same predetermined time interval in regions of the data stream resulting from partitioning acquired one or more of audio information and video information into lengths of partitioned data each corresponding to a predefined time interval and compressing the lengths of partitioned data, the acquired one or more of audio information and video information of the music performance being acquired at a performance at a given location, the body motion information indicative of the tempo of the music of the music performance and bio-information being of at least one individual present at the given location and being detected concurrent with the acquiring of the one or more of audio information and video information, the statistically processed body motion information indicative of the tempo of the music of the music performance and bio-information being generated by performing statistical processing of the detected body motion information indicative of the tempo of the music of the music performance and bio-information over predetermined time intervals corresponding to respective pluralities of the first data packets.

44. The recording medium as set forth in claim 43, wherein the at least one individual includes a speaker, a player, an actor, or a conductor who serves as a source of the audio information, and/or a performer or a photographed person who is included within the video information.

45. The recording medium as set forth in claim 43, wherein the at least one individual includes a listener present at the given location when the audio information is acquired and/or a viewer present at the given location when the video information is acquired.

46. The recording medium as set forth in claim 43, wherein the bio-information is selected from the group consisting of myoelectricity, body surface temperature, skin sweating, skin resistance, pulse, breath, micro-vibration, cardioelectricity, heartbeat, and blood pressure.

* * * * *